United States Patent
Zhang et al.

(10) Patent No.: US 11,175,274 B2
(45) Date of Patent: Nov. 16, 2021

(54) SYSTEMS AND METHODS FOR REMAINING USEFUL LIFE PREDICTION OF A FLUID

(71) Applicant: Caterpillar Inc., Deerfield, IL (US)

(72) Inventors: Yanchai Zhang, Dunlap, IL (US); Kyle Walton, Edelstein, IL (US); Richard Carpenter, Chillicothe, IL (US); Venkata Dandibhotla, Lakewood, CO (US); Baoyang Deng, Edwards, IL (US)

(73) Assignee: Caterpillar Inc., Peoria, IL (US)

( * ) Notice: Subject to any disclaimer, the term of this patent is extended or adjusted under 35 U.S.C. 154(b) by 256 days.

(21) Appl. No.: 16/429,851

(22) Filed: Jun. 3, 2019

(65) Prior Publication Data

US 2020/0378283 A1 Dec. 3, 2020

(51) Int. Cl.
*G01N 33/28* (2006.01)
*F01M 11/10* (2006.01)

(52) U.S. Cl.
CPC ......... *G01N 33/2888* (2013.01); *F01M 11/10* (2013.01); *F01M 2011/14* (2013.01); *F01M 2011/142* (2013.01); *F01M 2011/148* (2013.01); *F01M 2011/1413* (2013.01); *F01M 2011/1473* (2013.01); *F16N 2250/30* (2013.01); *F16N 2260/18* (2013.01)

(58) Field of Classification Search
None
See application file for complete search history.

(56) References Cited

U.S. PATENT DOCUMENTS

| | | | | |
|---|---|---|---|---|
| 4,620,185 A | * | 10/1986 | Plahmer | F16N 29/00 340/682 |
| 5,382,942 A | * | 1/1995 | Raffa | F01M 11/10 340/438 |
| 5,604,441 A | * | 2/1997 | Freese | G01N 27/221 324/663 |
| 6,023,961 A | * | 2/2000 | Discenzo | F16C 19/52 422/68.1 |
| 6,196,057 B1 | * | 3/2001 | Discenzo | F16C 19/52 73/54.01 |
| 6,253,601 B1 | | 7/2001 | Wang et al. | |
| 6,286,363 B1 | * | 9/2001 | Discenzo | G01N 11/16 340/631 |

(Continued)

OTHER PUBLICATIONS

Anveshan Bommareddi, "An Engine Oil Life Algorithm", Dec. 2009, 103 pages.

*Primary Examiner* — Kevin R Steckbauer
(74) *Attorney, Agent, or Firm* — Harrity & Harrity LLP

(57) ABSTRACT

A fluid degradation monitoring system may detect a replacement of a fluid of a machine. The fluid degradation monitoring system may determine, after detecting the replacement of the fluid, a first degradation estimate of the fluid using a first technique based on characteristics relating to an operation of the machine. The fluid degradation monitoring system may detect a transition in a value of a dielectric constant of the fluid from a first phase to a second phase. The fluid degradation monitoring system may determine, after detecting the transition in the value of the dielectric constant, a second degradation estimate of the fluid using a second technique based on characteristics relating to the fluid.

20 Claims, 4 Drawing Sheets

(56) References Cited

U.S. PATENT DOCUMENTS

| | | | |
|---|---|---|---|
| 6,324,899 B1 * | 12/2001 | Discenzo | F16C 19/52 |
| | | | 340/631 |
| 6,434,512 B1 * | 8/2002 | Discenzo | F16C 19/52 |
| | | | 702/184 |
| 6,509,749 B1 * | 1/2003 | Buelna | F01M 11/10 |
| | | | 324/698 |
| 6,513,367 B2 * | 2/2003 | Bondarowicz | G01N 33/2888 |
| | | | 324/672 |
| 6,546,785 B1 * | 4/2003 | Discenzo | F16C 19/52 |
| | | | 73/53.05 |
| 6,741,938 B2 | 5/2004 | Berndorfer | |
| 6,877,360 B1 * | 4/2005 | Discenzo | F16C 19/52 |
| | | | 73/53.05 |
| 7,493,799 B1 * | 2/2009 | Discenzo | F16C 19/52 |
| | | | 184/108 |
| 7,581,434 B1 * | 9/2009 | Discenzo | G01N 33/2888 |
| | | | 73/53.01 |
| 7,690,246 B1 * | 4/2010 | Discenzo | G01N 33/30 |
| | | | 73/53.05 |
| 7,835,875 B2 * | 11/2010 | Halalay | G01N 33/2888 |
| | | | 702/50 |
| 7,940,060 B2 * | 5/2011 | Halalay | G01N 33/2888 |
| | | | 324/698 |
| 9,038,448 B2 * | 5/2015 | Micali | G01N 33/22 |
| | | | 73/114.77 |
| 9,732,838 B2 * | 8/2017 | McKimpson | G01N 33/2888 |
| 9,804,142 B2 * | 10/2017 | Basu | G01N 33/2888 |
| 10,048,166 B2 * | 8/2018 | Micali | G01N 33/2888 |
| 10,323,597 B2 * | 6/2019 | Radue | G01N 33/2888 |
| 10,473,008 B2 * | 11/2019 | Zhang | E02F 9/267 |
| 10,725,015 B2 * | 7/2020 | Radue | F02M 35/0205 |
| 10,927,774 B2 * | 2/2021 | Cai | F02D 41/1406 |
| 2002/0112529 A1 * | 8/2002 | Bondarowicz | G01N 33/2888 |
| | | | 73/53.05 |
| 2002/0166366 A1 * | 11/2002 | Bondarowicz | G01N 33/2888 |
| | | | 73/53.05 |
| 2008/0302606 A1 * | 12/2008 | Alston | F01M 11/10 |
| | | | 184/6 |
| 2010/0250156 A1 * | 9/2010 | Halalay | G01N 33/2888 |
| | | | 702/50 |
| 2012/0062894 A1 * | 3/2012 | Micali | F16N 29/00 |
| | | | 356/436 |
| 2014/0123731 A1 * | 5/2014 | Basu | G01N 33/28 |
| | | | 73/38 |
| 2015/0192560 A1 | 7/2015 | Basu et al. | |
| 2015/0226640 A1 * | 8/2015 | Micali | F01M 1/08 |
| | | | 73/114.77 |
| 2017/0044942 A1 * | 2/2017 | Barnickel | F16H 57/0405 |
| 2017/0082188 A1 * | 3/2017 | McKimpson | F16H 57/0405 |
| 2017/0248092 A1 * | 8/2017 | Radue | F02D 41/22 |
| 2018/0231518 A1 * | 8/2018 | Vaidya | F01M 1/02 |
| 2019/0195097 A1 * | 6/2019 | Zhang | F01M 11/10 |
| 2019/0257260 A1 * | 8/2019 | Radue | G01N 33/2888 |
| 2020/0072137 A1 * | 3/2020 | Cai | F02D 41/26 |
| 2020/0309759 A1 * | 10/2020 | Radue | F02M 35/09 |
| 2020/0325657 A1 * | 10/2020 | Takami | F16N 29/04 |
| 2020/0378283 A1 * | 12/2020 | Zhang | F01M 11/10 |

* cited by examiner

SYSTEMS AND METHODS FOR REMAINING USEFUL LIFE PREDICTION OF A FLUID

TECHNICAL FIELD

The present disclosure relates generally to a fluid degradation monitoring system and, more particularly, to fluid degradation monitoring system for an engine of a machine.

BACKGROUND

Replacing engine fluids, such as engine oil, may reduce wear to an engine and extend a life of the engine. In some cases, replacement of engine fluids is in accordance with a set schedule, which may be based on factors such as engine mileage or an elapsed time from a previous replacement of the fluid. In other cases, replacement of engine fluids is based on a prediction of a remaining useful life of the fluid. For example, a fluid quality sensor may monitor characteristics of the fluid, such as viscosity, density, dielectric constant, and temperature, and predict a remaining useful life of the fluid based on the characteristics. However, typically, engine fluids contain additives for improving performance of the engine fluid. The additives may distort the characteristics of the fluid, thereby making accurate prediction of a remaining useful life of the fluid difficult.

One attempt to determine a remaining useful life of a fluid is disclosed in U.S. Pat. No. 7,581,434 that issued to Rockwell Automation Technologies, Inc. on Sep. 1, 2009 ("the '434 patent"). In particular, the '434 patent discloses three approaches for lubricant health monitoring and prognosis systems. A first approach disclosed by the '434 patent is a model-based approach, whereby oil degradation models are developed using data from oil and machine tests. The model may use data from sensors to estimate a remaining useful life of a machine and a lubricant. A second approach disclosed by the '434 patent is a sensor-based approach, whereby sensors directly measure a condition of a lubricant. A third approach disclosed by the '434 patent is a hybrid approach that is a combination of the model-based approach and the sensor-based approach.

While the lubricant health monitoring and prognosis systems of the '434 patent may use a combination of a model-based approach and a sensor-based approach for lubricant health monitoring and prognosis, the '434 patent does not suggest using the model-based approach during a first phase of an engine fluid lifecycle, when additives in the engine fluid are at a higher concentration, and using the sensor-based approach during a second phase of the engine fluid lifecycle, when additives in the engine fluid are at a lower concentration. Furthermore, the '434 patent does not suggest detecting a transition from the first phase of the engine fluid lifecycle to the second phase of the engine fluid lifecycle.

The fluid degradation monitoring system of the present disclosure solves one or more of the problems set forth above and/or other problems in the art.

SUMMARY

According to some implementations, the present disclosure is related to a method. The method may include detecting, by a device, a replacement of a fluid of a machine; determining, by the device and after detecting the replacement of the fluid, a first degradation estimate of the fluid using a first technique, wherein the first technique is based on one or more characteristics relating to an operation of the machine; providing, by the device, information identifying the first degradation estimate of the fluid; detecting, by the device, a transition in a value of a dielectric constant of the fluid from a first phase to a second phase, wherein the first phase is associated with a decrease in the value of the dielectric constant over a first time period and the second phase is associated with an increase in the value of the dielectric constant over a second time period; determining, by the device and after detecting the transition in the value of the dielectric constant, a second degradation estimate of the fluid using a second technique, wherein the second technique is based on one or more characteristics relating to the fluid; and providing, by the device, information identifying the second degradation estimate of the fluid.

According to some implementations, the present disclosure is related to a fluid degradation monitoring system. The fluid degradation monitoring system may include one or more memories, and one or more processors, communicatively coupled to the one or more memories, to: determine a first degradation estimate of a fluid of a machine using a first technique, wherein the first technique is based on one or more characteristics relating to an operation of the machine; detect a transition in a value of a dielectric constant of the fluid from a first phase to a second phase, wherein the first phase is associated with a decrease in the value of the dielectric constant over a first time period and the second phase is associated with an increase in the value of the dielectric constant over a second time period; and determine, after detecting the transition in the value of the dielectric constant, a second degradation estimate of the fluid using a second technique, wherein the second technique is based on one or more characteristics relating to the fluid.

According to some implementations, the present disclosure is related to a machine. The machine may include an engine, a display, and a fluid degradation monitoring system, wherein the fluid degradation monitoring system is to: detect a replacement of a fluid of the engine; determine, after detecting the replacement of the fluid, a first degradation estimate of the fluid using a first technique, wherein the first technique is based on one or more characteristics relating to an operation of the engine; provide information identifying the first degradation estimate of the fluid to the display; detect a transition in a value of a dielectric constant of the fluid from a first phase to a second phase, wherein the first phase is associated with a decrease in the value of the dielectric constant over a first time period and the second phase is associated with an increase in the value of the dielectric constant over a second time period; determine, after detecting the transition in the value of the dielectric constant, a second degradation estimate of the fluid using a second technique, wherein the second technique is based on one or more characteristics relating to the fluid; and provide information identifying the second degradation estimate of the fluid to the display.

DETAILED DESCRIPTION

This disclosure relates to a fluid degradation monitoring system. The fluid degradation monitoring system has universal applicability to any machine with an engine. The term "machine" may refer to any machine that performs an operation associated with an industry such as, for example, mining, construction, farming, transportation, or any other industry. As some examples, the machine may be a vehicle, a backhoe loader, a cold planer, a wheel loader, a compactor, a feller buncher, a forest machine, a forwarder, a harvester, an excavator, an industrial loader, a knuckleboom loader, a material handler, a motor grader, a pipelayer, a road reclaimer, a skid steer loader, a skidder, a telehandler, a tractor, a dozer, a tractor scraper, or other above ground equipment, underground equipment, or marine equipment.

Figure 1:
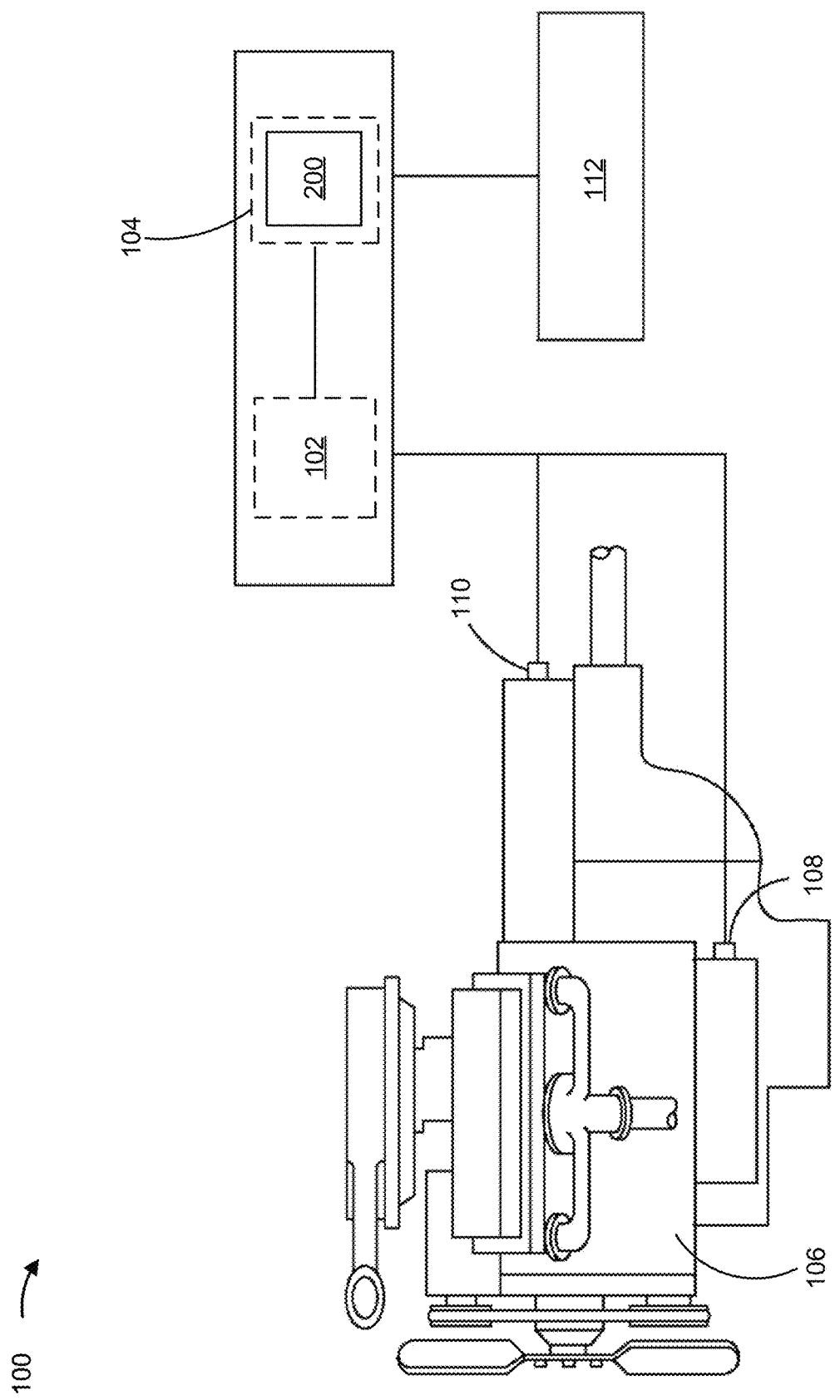
FIG. 1 is diagram of example components described herein.

FIG. 1 is a diagram of example components 100 described herein. As shown in FIG. 1, components 100 may include a fluid degradation monitoring system 200 that is associated with an engine 106 and a display 112. Fluid degradation monitoring system 200, engine 106, and display 112 may be components of a machine (not shown).

Fluid degradation monitoring system 200 may determine an estimate of an amount of degradation of a fluid. For example, fluid degradation monitoring system 200 may determine an estimate of an amount of degradation of a fluid in order to predict a remaining useful life of the fluid (e.g., as a percentage of a useful life that is remaining, as a time of a useful life that is remaining, and/or the like). The fluid may be an engine fluid, such as an engine oil (e.g., a mineral engine oil or a synthetic engine oil) or another engine lubricant. In some implementations, the fluid may be a transmission fluid, a radiator fluid, a brake fluid, a power-steering fluid, and/or the like.

Figure 2:
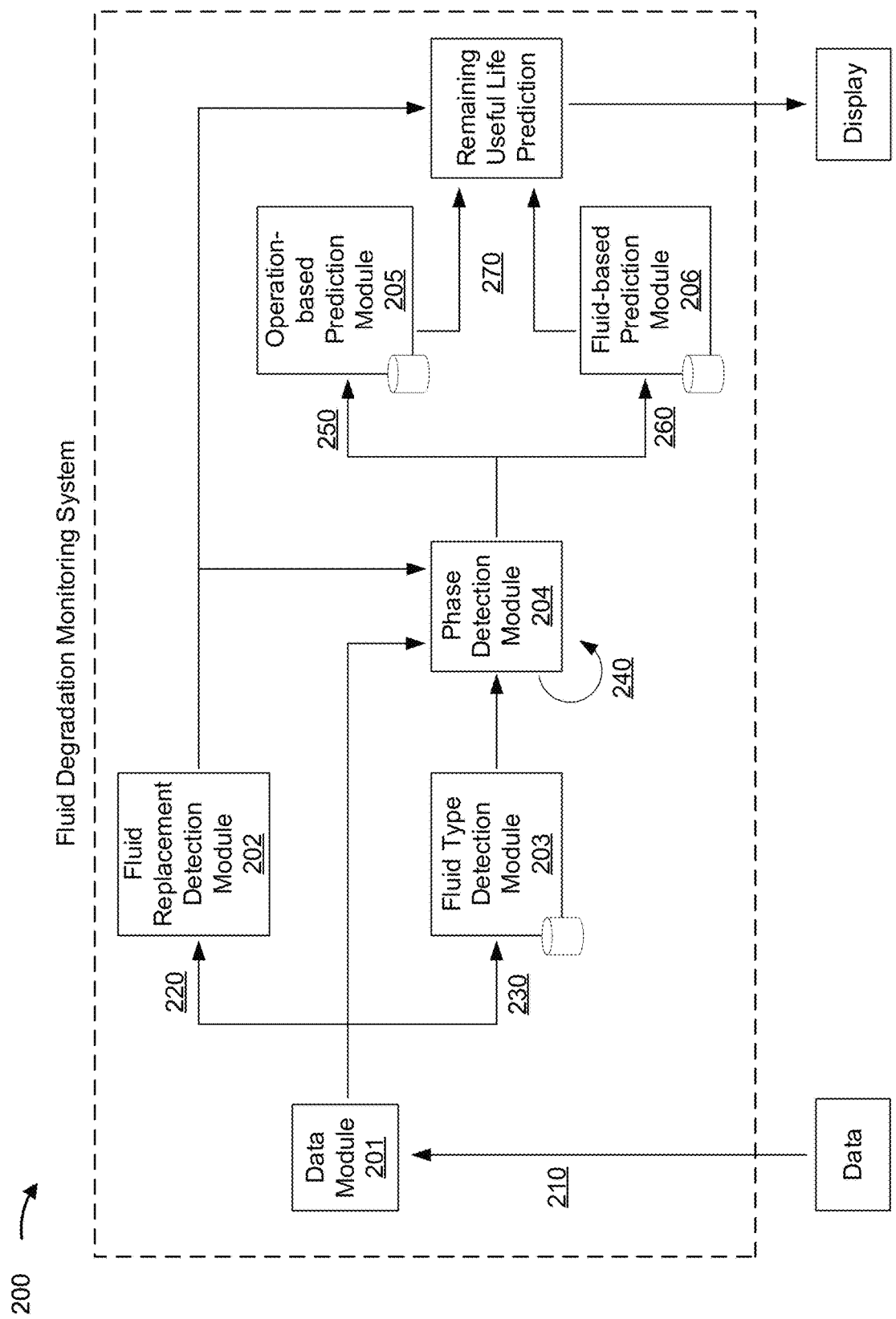
FIG. 2 is diagram of an example fluid degradation monitoring system described herein.

Fluid degradation monitoring system 200 may be implemented by a processor 102 and a memory 104. Processor 102 may be implemented in hardware, firmware, and/or a combination of hardware and software. Processor 102 may be a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. Processor 102 may include one or more processors capable of being programmed to perform a function. Memory 104 may include a random-access memory (RAM), a read only memory (ROM), and/or another type of dynamic or static storage device (e.g., a flash memory, a magnetic memory, and/or an optical memory) that stores information and/or instructions for use by processor 102 (e.g., information and/or instructions associated with data module 201, fluid replacement detection module 202, fluid type detection module 203, phase detection module 204, operation-based prediction module 205, and/or fluid-based prediction module 206 of fluid degradation monitoring system 200, as shown in FIG. 2).

Engine 106 may be an electric engine or a combustion engine (e.g., a diesel engine, a gasoline engine, or a dual-fuel engine). Engine 106 may be coupled with a transmission system (not shown) to drive the machine (not shown). In some implementations, engine 106 may include an engine control module (ECM) (not shown) that implements fluid degradation monitoring system 200 or one or more modules thereof.

Engine 106 may be associated with one or more sensors 108 configured to detect and measure characteristics relating to an operation of engine 106. For example, sensors 108 may detect and measure characteristics relating to a speed (e.g., a rotational speed) of engine 106, a load on engine 106, a temperature (e.g., a temperature of air, exhaust, a component, coolant, and/or the like) of engine 106, a pressure (e.g., a brake mean effective pressure) of engine 106, and/or the like. Accordingly, sensors 108 may include one or more load sensors, speed sensors, pressure sensors, temperature sensors (e.g., thermocouple junctions), emission sensors, and/or the like.

Engine 106 also may be associated with one or more sensors 110 configured to detect and measure characteristics relating to a fluid of engine 106. For example, sensors 110 may detect and measure characteristics relating to a viscosity of the fluid, a density of the fluid, a dielectric constant of the fluid, a temperature of the fluid, a pressure of the fluid, and/or the like. Accordingly, sensors 110 may include one or more weight sensors, volume sensors, density sensors, viscosity sensors, temperature sensors, pressure sensors, capacitance sensors, and/or the like. For example, sensors 110 may include one or more oil quality sensors. Sensors 108 and/or sensors 110 may be associated with an analog-to-digital converter (not shown) for converting analog signals into digital form.

Display 112 may receive information identifying an estimate of an amount of degradation of a fluid and/or a remaining useful life of the fluid (e.g., from fluid degradation monitoring system 200). Display 112 may present (e.g., in a graphical user interface) data relating to the degradation of the fluid and/or the remaining useful life of the fluid. The data may include one or more graphs, charts, percentages, countdowns, and/or the like. Display 112 may be associated with an onboard computer of the machine, an aftermarket display for use with the machine, a user device (e.g., a smart phone, a tablet computer, a laptop computer, a desktop computer, and/or the like), and/or the like.

As indicated above, FIG. 1 is provided as an example. Other examples may differ from what is described in connection with FIG. 1.

FIG. 2 is a diagram of an example fluid degradation monitoring system 200 in which systems and/or methods described herein may be implemented. As shown in FIG. 2, fluid degradation monitoring system 200 may include a data module 201, a fluid replacement detection module 202, a fluid type detection module 203, a phase detection module 204, an operation-based prediction module 205, and a fluid-based prediction module 206.

As shown by reference number 210, fluid degradation monitoring system 200 may obtain data relating to an operation of an engine (e.g., engine 106) and/or a fluid of the engine. For example, data module 201 of fluid degradation monitoring system 200 may obtain data relating to the operation of the engine and/or the fluid of the engine. Data module 201 may obtain the data from one or more sensors of the engine configured to measure characteristics relating to an operation of the engine (e.g., sensors 108) and/or one or more sensors of the engine configured to measure characteristics relating to a fluid of the engine (e.g., sensors 110). Data module 201 may obtain the data as a data stream (e.g., a time series), or alternatively, data module 201 may obtain the data at regular intervals (e.g., 5 second intervals, 30 second intervals, and/or the like) or irregular intervals (e.g., when the engine is started, when the engine changes states, and/or the like).

Data module 201 may process the data in order to filter the data, remove noise from the data, normalize the data, sample the data (e.g., to reduce a size of the data), and/or the like. For example, data module 201 may process the data with a low-pass filter to remove noise from the data. As another example, data module 201 may normalize viscosity measurements and/or dielectric constant measurements according to corresponding temperature measurements. As a further example, data module 201 may process viscosity measurements and density measurements to calculate a kinematic viscosity.

As shown by reference number 220, fluid replacement detection module 202 of fluid degradation monitoring system 200 may obtain the data (e.g., data relating to an operation of the engine and/or a fluid of the engine) from data module 201. Based on the data, fluid replacement detection module 202 may detect whether a fluid of the engine was replaced (e.g., an engine oil change). In other words, fluid replacement detection module 202 may compare the data to previous data to detect whether a fluid of the engine was replaced.

Fluid replacement detection module 202 may detect whether a fluid of the engine was replaced based on data relating to a density of a fluid. For example, as engine oil degrades, a density of the engine oil increases. Accordingly, fluid replacement detection module 202 may determine whether a current density measurement of a fluid is less than one or more previous density measurements of the fluid in order to detect a replacement of the fluid. For example, fluid replacement detection module 202 may determine whether a change in density measurements of a fluid (e.g., a downward change from a previous measurement to a current measurement) satisfies a threshold value in order to detect a replacement of the fluid.

Based on detecting a replacement of a fluid of the engine, fluid replacement detection module 202 may perform one or more actions. For example, fluid replacement detection module 202 may provide information identifying the replacement of the fluid to phase detection module 204, as described below. As another example, fluid replacement detection module 202 may provide (e.g., to a display) a remaining useful life prediction for the fluid indicating a full remaining useful life of the fluid. The full remaining useful life may be expressed as a percentage of useful life remaining (e.g., 100%) or as a time of useful life remaining (e.g., 500 hours), which may be based on a known useful life of the fluid (e.g., according to experimental data).

As shown by reference number 230, fluid type detection module 203 of fluid degradation monitoring system 200 also may obtain the data (e.g., data relating to an operation of the engine and/or a fluid of the engine) from data module 201. Based on the data, fluid type detection module 203 may detect a type of a fluid of the engine. In some implementations, fluid type detection module 203 may detect a type of a fluid and provide the type to fluid replacement detection module 202 to permit fluid replacement detection module 202 to detect a replacement of the fluid based on the type (e.g., a particular type of fluid may have a particular density change threshold value indicative of a replacement). Alternatively, fluid type detection module 203 may detect a type of a fluid upon receiving an indication of a fluid replacement from fluid replacement detection module 202.

Fluid type detection module 203 may detect a type of a fluid as a class of the fluid (e.g., engine oil, transmission fluid, power steering fluid, and/or the like) and/or a grade of the fluid (e.g., 5 W-20, 10 W-30, and/or the like). Fluid type detection module 203 may detect a type of a fluid based on data relating to a viscosity of the fluid. As viscosity of a fluid is dependent on temperature, fluid type detection module 203 also may obtain data relating to a temperature of the fluid. Fluid type detection module 203 may normalize a viscosity measurement according to a corresponding temperature measurement and compare the normalized viscosity measurement to a mapping of viscosities to fluid types. The mapping may be based on experimental data relating to viscosities of fluid types at a reference temperature. Fluid type detection module 203 and/or fluid degradation monitoring system 200 may store the mapping in a data structure (e.g., a database, a linked list, a table, and/or the like).

Fluid type detection module 203 may determine whether a type of a fluid detected is incompatible with the engine or the machine. For example, fluid type detection module 203 may detect that a type of a fluid is transmission fluid and determine that the transmission fluid is incompatible with the engine. As another example, fluid type detection module 203 may detect that a type of a fluid is a particular grade of engine oil and determine that the particular grade of engine oil is incompatible with the engine. Accordingly, fluid type detection module 203 and/or fluid degradation monitoring system 200 may store information relating to fluid tolerances of the engine and/or the machine, which may be used to determine whether a type of a fluid is incompatible with the engine or the machine.

Based on detecting an incompatible type of fluid, fluid type detection module 203 may perform one or more actions. For example, fluid type detection module 203 may cause an alert to be transmitted to a display (e.g., display 112), to a user device, and/or the like. As another example, fluid type detection module 203 may cause an ignition of the machine to be disabled, the engine of the machine to be disabled, and/or the like.

As shown by reference number 240, phase detection module 204 of fluid degradation monitoring system 200 also may obtain the data (e.g., data relating to an operation of the engine and/or a fluid of the engine) from data module 201. In addition, phase detection module 204 may obtain data from fluid replacement detection module 202 relating to a replacement of a fluid, as described above, and/or data from fluid type detection module 203 relating to a type of a fluid, as described above. Based on the obtained data, phase detection module 204 may determine a phase in a lifecycle of a fluid. In other words, phase detection module 204 may detect a transition from a first phase in a lifecycle of a fluid to a second phase in the lifecycle of the fluid.

As described above, a fluid, such as engine oil, may contain additives (e.g., lubrication additives) to improve a performance of the fluid. A first phase in the lifecycle of a fluid may correspond to a relatively high concentration of the additives in the fluid. For example, the concentration of the additives may be above a threshold value at which estimating a degradation of the fluid according to characteristics of the fluid is inaccurate. A second phase in the lifecycle of the fluid may correspond to a relatively low concentration of the additives in the fluid (e.g., less than 10%, less than 1%, less than 0.1%, less than 0.01%, and/or the like). For example, the concentration of the additives may be below the threshold value. Accordingly, phase detection module 204 may monitor measurements relating to a concentration of additives in a fluid and detect the transition from the first phase to the second phase when the concentration crosses the threshold value.

Additionally, or alternatively, phase detection module 204 may detect the transition from the first phase to the second phase based on data relating to a dielectric constant of a fluid (or another characteristic of the fluid, such as viscosity, density, and/or the like). For example, during the first phase, a value of the dielectric constant may decrease, and during the second phase, the value of the dielectric constant may increase. Accordingly, phase detection module 204 may monitor measurements of the dielectric constant over a time period to detect a transition from decreasing values of the dielectric constant to increasing values of the dielectric constant. Similarly, phase detection module 204 may monitor measurements of the dielectric constant over a time period and fit a curve to measured values of the dielectric constant. Phase detection module 204 may detect the transition from the first phase to the second phase when a slope of the curve transitions from a decreasing slope to an increasing slope.

The first phase may be associated with a first time period and the second phase may be associated with a second time period. The first time period may begin upon a replacement of a fluid (e.g., upon a replacement of a fluid detected by fluid replacement detection module 202) and have a duration of about 150-200 operating hours of the engine. The second time period may begin after the first time period and continue until a subsequent replacement of the fluid. In some implementations, phase detection module 204 may determine the transition from the first phase to the second phase according to a transition from the first time period to the second time period. For example, phase detection module 204 may initiate a timer upon a replacement of a fluid (e.g., upon a replacement of a fluid detected by fluid replacement detection module 202) and determine the transition when a threshold amount of engine operating time (e.g., 150-200 hours) has elapsed. The threshold amount of engine operating time may be particular to a type of a fluid (e.g., a type of a fluid detected by fluid type detection module 203) and determined according to experimental data.

Based on detecting the transition from the first phase to the second phase, phase detection module 204 may perform one or more actions. For example, phase detection module 204 may set a flag indicating that a lifecycle of the fluid is in the second phase. In such a case, phase detection module 204 may discontinue phase detection while the flag indicates that the lifecycle of the fluid is in the second phase. As described above, phase detection module 204 may receive, from fluid replacement detection module 202, an indication that a fluid has been replaced. In such a case, phase detection module 204 may reset the flag to indicate that the lifecycle of the fluid is in the first phase.

As another action, phase detection module 204 may designate one of operation-based prediction module 205 or fluid-based prediction module 206 for estimating an amount of degradation of a fluid. For example, phase detection module 204 may determine the designation based on the phase detected by phase detection module 204 (e.g., based on the flag set by phase detection module 204).

As shown by reference number 250, operation-based prediction module 205 may determine an estimate of an amount of degradation of a fluid when a lifecycle of the fluid is in the first phase (e.g., before a transition is detected). For example, operation-based prediction module 205 may obtain data relating to an operation of the engine or the machine from phase detection module 204 and/or data module 201. Operation-based prediction module 205 may determine the estimate based on one or more characteristics relating to an operation of the engine and/or the machine. For example, operation-based prediction module 205 may determine the estimate based on measurements relating to a speed (e.g., a rotational speed) of the engine, a load on the engine, a temperature of the engine, a pressure (e.g., a brake mean effective pressure) in the engine, an operating time of the engine, a type of the machine, a use of the machine, and/or the like.

Operation-based prediction module 205 may determine the estimate by determining an expected useful life of a fluid based on a type of the fluid (e.g., a type of the fluid detected by fluid type detection module 203), a type of the engine, and/or an expected use of the machine. For example, the expected useful life may be determined based on experimental data relating to particular types of fluids, particular types of engines, and particular uses of the machine.

Operation-based prediction module 205 may adjust the expected useful life of the fluid based on data relating to operating conditions of the engine, such as speed data, load data, temperature data, pressure data, and/or the like. For example, engine speed measurements outside of an optimal range (e.g., engine speed measurements higher or lower than the optimal range) may result in a larger reduction of the expected useful life than engine speed measurements within the optimal range (e.g., which may result in no reduction of the expected useful life). An amount of an adjustment to the expected useful life may be based on degradation rate factors, which may be determined according to experimental data. For example, operation-based prediction module 205 may apply a degradation rate factor relating to engine speed to speed data, a degradation rate factor relating to engine load to load data, a degradation rate factor relating to engine temperature to temperature data, and/or a degradation rate factor relating to engine pressure to pressure data.

Operation-based prediction module 205 and/or fluid degradation monitoring system 200 may store information related to determining an expected useful life (e.g., a mapping of weightings to fluid types, engine types, and/or machine uses) and/or degradation rate factors (e.g., degradation rate factors for speed data, load data, temperature data, and/or pressure data) in a data structure (e.g., a database, a linked list, a table, and/or the like).

Operation-based prediction module 205 may determine an estimate of an amount of degradation of a fluid using a procedure other than that described herein. For example, operation-based prediction module 205 may employ any procedure capable of determining an estimate of an amount of degradation of a fluid that does not use measurements (e.g., sensor measurements) relating to characteristics of a fluid.

As shown by reference number 260, fluid-based prediction module 206 may determine an estimate of an amount of degradation of a fluid when a lifecycle of the fluid is in the second phase (e.g., after a transition is detected). For example, fluid-based prediction module 206 may obtain data relating to a fluid of the engine from phase detection module 204 and/or data module 201. Fluid-based prediction module 206 may determine the estimate based on one or more characteristics relating to the fluid. For example, fluid-based prediction module 206 may determine the estimate based on measurements relating to a viscosity of the fluid, a density of the fluid, a dielectric constant of the fluid, a temperature of the fluid, and/or the like.

In some implementations, fluid-based prediction module 206 may determine the estimate based on measurements (e.g., fluid quality sensor measurements) relating to a dielectric constant of the fluid. For example, fluid-based prediction module 206 may utilize a mapping of dielectric constants to levels of oxidation (e.g., a mapping that corresponds to a type of fluid detected by fluid type detection module 203) to determine an amount of degradation of the fluid. In such a case, a particular level of oxidation may relate to a particular amount of degradation, which may be determined based on experimental data. Fluid-based prediction module 206 and/or fluid degradation monitoring system 200 may store the mapping in a data structure (e.g., a database, a linked list, a table, and/or the like).

Fluid-based prediction module 206 may determine an estimate of an amount of degradation of a fluid using a procedure other than that described herein. For example, fluid-based prediction module 206 may employ any procedure capable of determining an estimate of an amount of degradation of a fluid that uses measurements (e.g., sensor measurements) relating to characteristics of a fluid.

As shown by reference number 270, operation-based prediction module 205 and/or fluid-based prediction module 206 may provide a remaining useful life prediction of a fluid based on an estimate of an amount of degradation of the fluid. In some implementations, operation-based prediction module 205 and/or fluid-based prediction module 206 may provide the estimate of the amount of degradation of the fluid, and another component of fluid degradation monitoring system 200 may determine a remaining useful life prediction of the fluid based on the estimate. The remaining useful life prediction may be provided to a display of the machine (e.g., display 112), to a user device, and/or the like. Fluid degradation monitoring system 200 may determine updates to the remaining useful life prediction as additional measurements (e.g., measurements relating to an operation of the engine and/or the fluid) are obtained and provide the updates to the display and/or to the user device (e.g., at regular intervals, such as 5 second intervals, 30 second intervals, and/or the like).

Fluid degradation monitoring system 200 may perform one or more additional actions when a remaining useful life prediction of a fluid satisfies a threshold value. For example, fluid degradation monitoring system 200 may display on a display of the machine, or transmit to a user device, an alert indicating that replacement of the fluid is recommended, indicating an amount of mileage or an amount of operating time of the machine until replacement of the fluid is recommended, and/or the like. As another example, fluid degradation monitoring system 200 may limit operating parameters of the machine (e.g., limit a maximum speed of the machine, limit a maximum load on the engine, and/or the like) in order to prolong a useful life of the fluid and/or the machine.

As indicated above, FIG. 2 is provided as an example. Other examples may differ from what is described in connection with FIG. 2.

Figure 3:
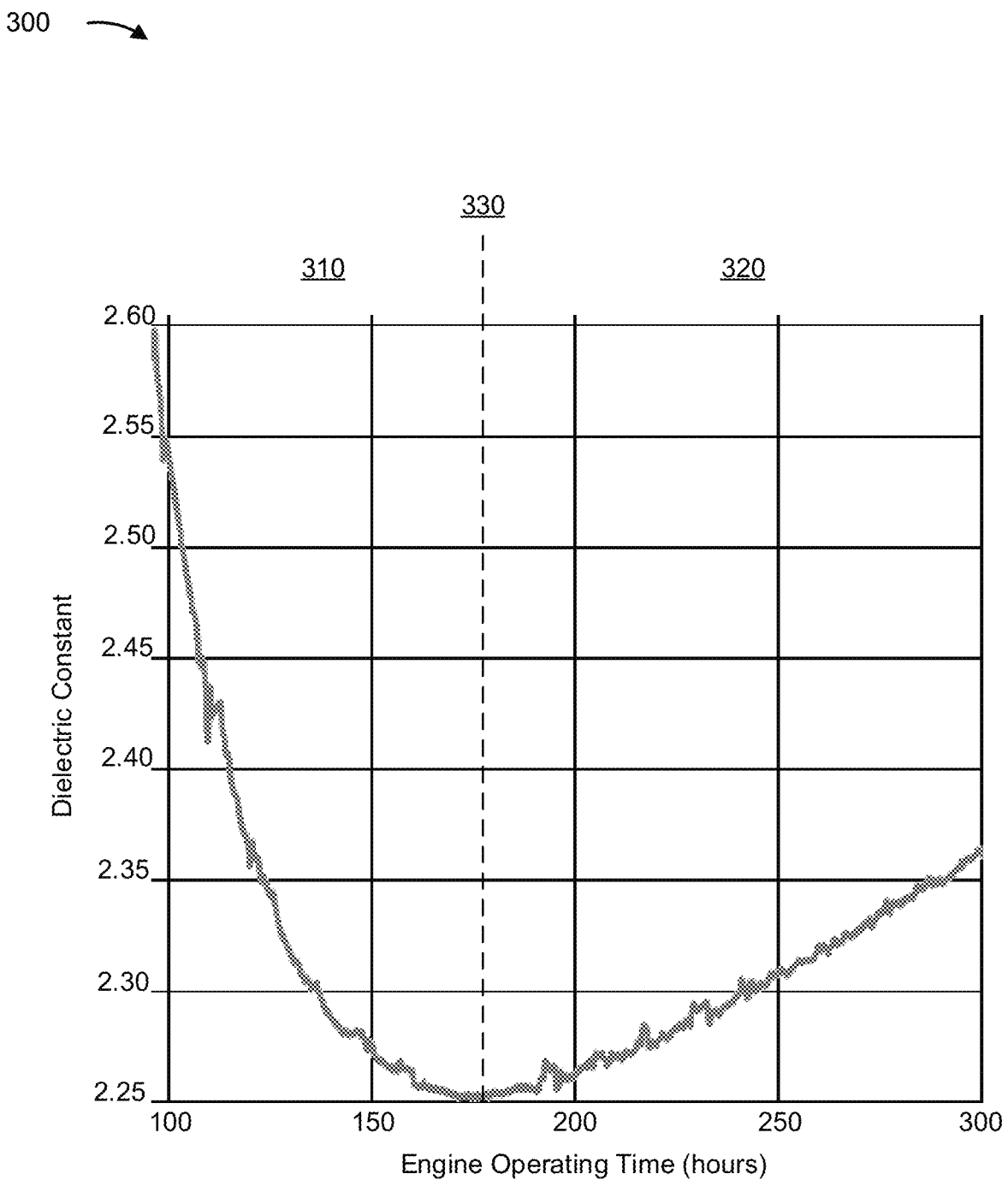
FIG. 3 is a diagram of an example representation of data that may be used by the fluid degradation monitoring system of FIG. 2, as described herein.

FIG. 3 is a diagram of an example representation of data 300 that may be used by fluid degradation monitoring system 200. As shown in FIG. 3, data 300 may include measurements relating to a dielectric constant of a fluid over a time period. The time period may relate to an operating time of an engine associated with the fluid.

As shown in FIG. 3, data 300 includes a first phase 310, a second phase 320, and a transition 330 from first phase 310 to second phase 320. First phase 310 is associated with a value of the dielectric constant that is decreasing over a first time period. In other words, a slope of a curve fitted to the value of the dielectric constant over the first time period is decreasing. Second phase 320 is associated with a value of the dielectric constant that is increasing over a second time period. In other words, a slope of a curve fitted to the value of the dielectric constant over the second time period is increasing. Transition 330 is associated with a change in the dielectric constant from a decreasing value to an increasing value. That is, transition 330 is associated with a transition in a slope of a value of the dielectric constant from a decreasing slope to an increasing slope.

As indicated above, FIG. 3 is provided as an example. Other examples may differ from what is described in connection with FIG. 3.

Figure 4:
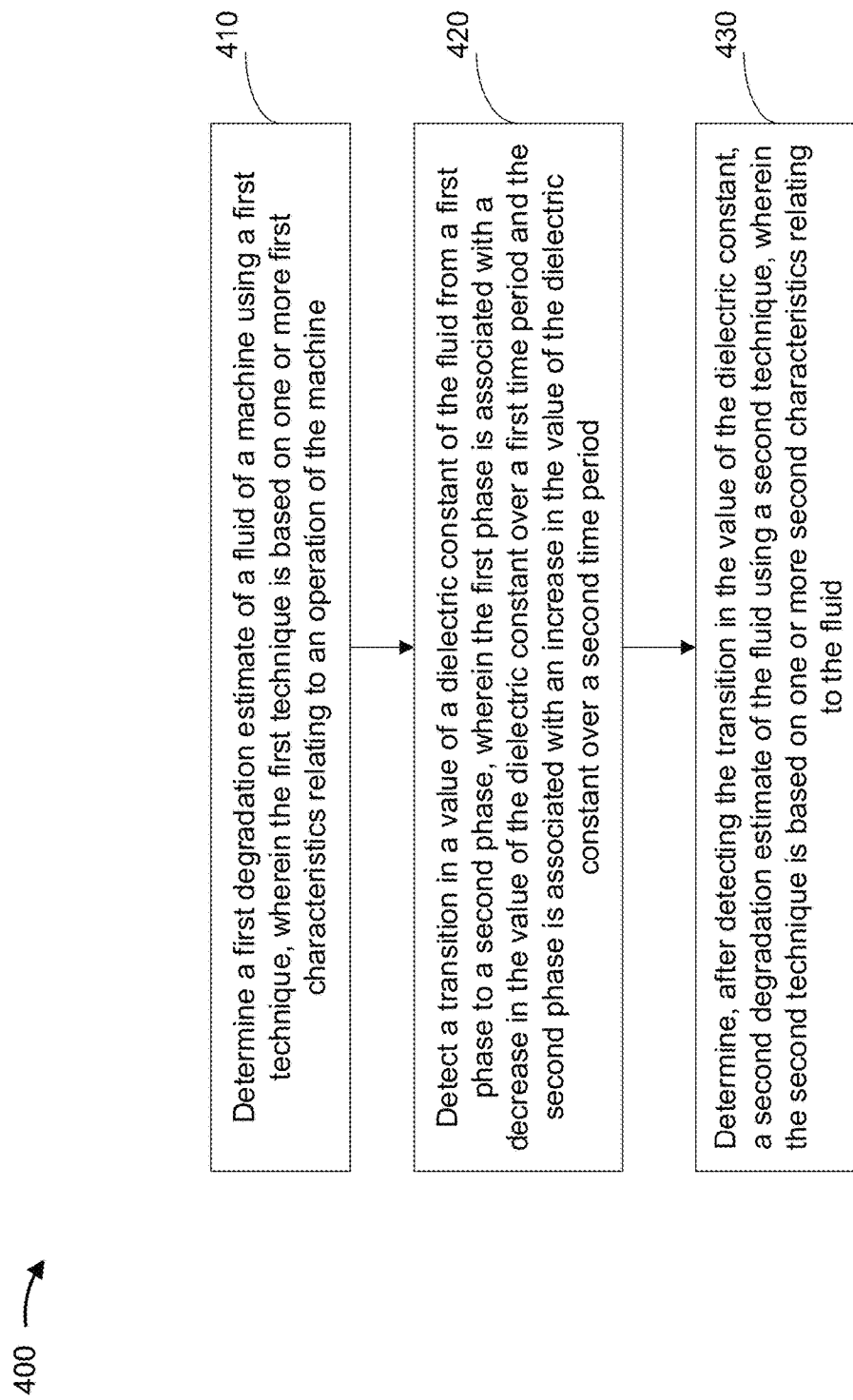
FIG. 4 is a flow chart of an example process for remaining useful life prediction of a fluid.

FIG. 4 is a flow chart of an example process 400 for remaining useful life prediction of a fluid. One or more process blocks of FIG. 4 may be performed by a fluid degradation monitoring system (e.g., fluid degradation monitoring system 200). Additionally, or alternatively, one or more process blocks of FIG. 4 may be performed by another device or a group of devices separate from or including the fluid degradation monitoring system, such as an ECM associated with an engine (e.g., an ECM associated with engine 106) and/or another device or component that is internal or external to a machine that includes the fluid degradation monitoring system.

As shown in FIG. 4, process 400 may include determining a first degradation estimate of a fluid of a machine using a first technique, wherein the first technique is based on one or more characteristics relating to an operation of the machine (block 410). For example, the fluid degradation monitoring system (e.g., using processor 102, memory 104, operation-based prediction module 205, and/or the like) may determine a first degradation estimate of a fluid of a machine using a first technique, as described above. The first technique may be based on one or more characteristics relating to an operation of the machine.

As further shown in FIG. 4, process 400 may include detecting a transition in a value of a dielectric constant of the fluid from a first phase to a second phase, wherein the first phase is associated with a decrease in the value of the dielectric constant over a first time period and the second phase is associated with an increase in the value of the dielectric constant over a second time period (block 420). For example, the fluid degradation monitoring system (e.g., using processor 102, memory 104, phase detection module 204, and/or the like) may detect a transition in a value of a dielectric constant of the fluid from a first phase to a second phase, as described above. The first phase may be associated with a decrease in the value of the dielectric constant over a first time period and the second phase may be associated with an increase in the value of the dielectric constant over a second time period.

As further shown in FIG. 4, process 400 may include determining, after detecting the transition in the value of the dielectric constant, a second degradation estimate of the fluid using a second technique, wherein the second technique is based on one or more characteristics relating to the fluid (block 430). For example, the fluid degradation monitoring system (e.g., using processor 102, memory 104, fluid-based prediction module 206, and/or the like) may determine, after detecting the transition in the value of the dielectric constant, a second degradation estimate of the fluid using a second technique, as described above. The second technique may be based on one or more characteristics relating to the fluid.

Process 400 may include additional implementations, such as any single implementation or any combination of implementations described below and/or in connection with one or more other processes described elsewhere herein.

For example, the fluid may be an engine lubricant. In addition, the fluid degradation monitoring system may detect a type of the fluid. Accordingly, the first technique may be based on the one or more characteristics relating to the operation of the machine and based on the type of the fluid, and the second technique may be based on the one or more characteristics relating to the fluid and based on the type of the fluid. The fluid degradation monitoring system, when detecting the type of the fluid, may detect the type of the fluid based on a viscosity of the fluid.

The one or more characteristics relating to the operation of the machine may include one or more of a speed of an engine of the machine, a load on the engine of the machine, or a temperature of the engine of the machine. The one or more characteristics relating to the fluid may include one or more of a viscosity of the fluid, a density of the fluid, the dielectric constant of the fluid, or a temperature of the fluid. The first degradation estimate of the fluid and the second degradation estimate of the fluid may provide an estimate of a remaining useful life of the fluid.

The fluid degradation monitoring system may provide information identifying the first degradation estimate of the fluid to a display of the machine. The fluid degradation monitoring system may provide information identifying the second degradation estimate of the fluid to the display of the machine.

Additionally, or alternatively, a process may include detecting a replacement of a fluid of an engine. For example, the fluid degradation monitoring system (e.g., using processor 102, memory 104, fluid replacement detection module 202, and/or the like) may detect a replacement of a fluid of an engine, as described above.

Such a process may include determining, after detecting the replacement of the fluid, a first degradation estimate of the fluid using a first technique, wherein the first technique is based on one or more characteristics relating to an operation of an engine. For example, the fluid degradation monitoring system (e.g., using processor 102, memory 104, operation-based prediction module 205, and/or the like) may determine, after detecting the replacement of the fluid, a first degradation estimate of the fluid using a first technique, as described above. The first technique may be based on one or more characteristics relating to an operation of the engine.

Such a process may include providing information identifying the first degradation estimate of the fluid. For example, the fluid degradation monitoring system (e.g., using processor 102, memory 104, operation-based prediction module 205, and/or the like) may provide information identifying the first degradation estimate of the fluid, as described above.

Such a process may include detecting a transition in a value of a dielectric constant of the fluid from a first phase to a second phase, wherein the first phase is associated with a decrease in the value of the dielectric constant over a first time period, and the second phase is associated with an increase in the value of the dielectric constant over a second time period. For example, the fluid degradation monitoring system (e.g., using processor 102, memory 104, phase detection module 204, and/or the like) may detect a transition in a value of a dielectric constant of the fluid from a first phase to a second phase, as described above. The first phase may be associated with a decrease in the value of the dielectric constant over a first time period and the second phase may be associated with an increase in the value of the dielectric constant over a second time period.

Such a process may include determining, after detecting the transition in the value of the dielectric constant, a second degradation estimate of the fluid using a second technique, wherein the second technique is based on one or more characteristics relating to the fluid. For example, the fluid degradation monitoring system (e.g., using processor 102, memory 104, fluid-based prediction module 206, and/or the like) may determine, after detecting the transition in the value of the dielectric constant, a second degradation estimate of the fluid using a second technique, as described above. The second technique may be based on one or more characteristics relating to the fluid.

Such a process may include providing information identifying the second degradation estimate of the fluid. For example, the fluid degradation monitoring system (e.g., using processor 102, memory 104, fluid-based prediction module 206, and/or the like) may provide information identifying the second degradation estimate of the fluid, as described above.

Such a process may include additional implementations, such as any single implementation or any combination of implementations described below and/or in connection with one or more other processes described elsewhere herein.

For example, the fluid degradation monitoring system may be associated with an engine control module of the engine. In addition, the fluid may be an engine oil.

The one or more characteristics relating to the operation of the engine may include one or more of a speed of an engine, a load on the engine, or a temperature of the engine. The one or more characteristics relating to the fluid may include one or more of a viscosity of the fluid, a density of the fluid, the dielectric constant of the fluid, or a temperature of the fluid. The one or more characteristics relating to the operation of the engine may be obtained from one or more first sensors associated with the engine. The one or more characteristics relating to the fluid may be obtained from one or more second sensors associated with the fluid.

The fluid degradation monitoring system, when detecting the replacement of the fluid of the engine, may detect the replacement of the fluid of the engine based on a density decrease of the fluid that satisfies a threshold value.

The first phase may be associated with a first concentration of additives in the fluid and the second phase may be associated with a second concentration of additives in the fluid. The first concentration may be greater than the second concentration. Furthermore, a curve that is fit to the value of the dielectric constant may have a decreasing slope over the first time period and may have an increasing slope over the second time period.

The fluid degradation monitoring system, when providing the information identifying the first degradation estimate of the fluid, may provide the information identifying the first degradation estimate of the fluid to at least one of a display or a user device. The fluid degradation monitoring system, when providing the information identifying the second degradation estimate of the fluid, may provide the information identifying the second degradation estimate of the fluid to at least one of a display or a user device.

INDUSTRIAL APPLICABILITY

The disclosed fluid degradation monitoring system 200 may be used with any machine where improved prediction of a remaining useful life of a fluid is desired. During a first phase of a fluid's lifecycle, the fluid contains a high concentration of additives, which causes inaccurate prediction of a remaining useful life of the fluid using fluid quality sensors. The disclosed fluid degradation monitoring system 200 may estimate a degradation of a fluid based on characteristics relating to an operation of an engine associated with the fluid (e.g., without using fluid quality sensors) during the first phase of the fluid's lifecycle. In this way, during the first phase of the fluid's lifecycle, a remaining useful life of the fluid can be predicted with greater accuracy than a prediction that uses a fluid quality sensor. Accordingly, premature fluid replacement, which increases machine downtime and wastes useful fluid, as well as overdue fluid replacement, which increases wear to the engine and shortens a life of the engine, can be avoided.

During a second phase of the fluid's lifecycle, the fluid contains a low concentration of additives. The disclosed fluid degradation monitoring system 200 may estimate a degradation of the fluid based on characteristics relating to the fluid during the second phase of the fluid's lifecycle (e.g., using fluid quality sensors). In this way, a remaining useful life of the fluid can be accurately predicted during the second phase of the fluid's lifecycle using a fluid quality sensor, which provides efficient and computationally-light-weight prediction.

As used herein, the articles "a" and "an" are intended to include one or more items, and may be used interchangeably with "one or more." Also, as used herein, the terms "has," "have," "having," or the like are intended to be open-ended terms. Further, the phrase "based on" is intended to mean "based, at least in part, on."

The foregoing disclosure provides illustration and description, but is not intended to be exhaustive or to limit the implementations to the precise form disclosed. Modifications and variations may be made in light of the above disclosure or may be acquired from practice of the implementations. It is intended that the specification be considered as an example only, with a true scope of the disclosure being indicated by the following claims and their equivalents. Even though particular combinations of features are recited in the claims and/or disclosed in the specification, these combinations are not intended to limit the disclosure of various implementations. Although each dependent claim listed below may directly depend on only one claim, the disclosure of various implementations includes each dependent claim in combination with every other claim in the claim set.

What is claimed is:

1. A method, comprising:
   detecting a replacement of a fluid of a machine;
   determining, and after detecting the replacement of the fluid, a first degradation estimate of the fluid using a first technique,
      wherein the first technique is based on one or more characteristics relating to an operation of the machine;
   providing information identifying the first degradation estimate of the fluid;
   detecting a transition in a value of a dielectric constant of the fluid from a first phase to a second phase based on an average of the value of the dielectric constant decreasing over a first time period of the first phase and the average of the value of the dielectric constant increasing over a second time period of the second phase;
   determining, and after detecting the transition in the value of the dielectric constant, a second degradation estimate of the fluid using a second technique,
      wherein the second technique is based on one or more characteristics relating to the fluid; and
   providing information identifying the second degradation estimate of the fluid.

2. The method of claim 1, wherein the one or more characteristics relating to the operation of the machine include one or more of:
   a speed of an engine of the machine,
   a load on the engine of the machine, or
   a temperature of the engine of the machine,
   wherein the one or more characteristics relating to the fluid include one or more of:
   a viscosity of the fluid,
   a density of the fluid,
   the dielectric constant of the fluid, or
   a temperature of the fluid.

3. The method of claim 1, wherein the fluid is an engine oil.

4. The method of claim 1, wherein detecting the replacement of the fluid of the machine comprises:
   detecting the replacement of the fluid of the machine based on a density decrease of the fluid that satisfies a threshold value.

5. The method of claim 1, wherein the first phase is associated with a first concentration of additives in the fluid and the second phase is associated with a second concentration of additives in the fluid,
   wherein the first concentration is greater than the second concentration.

6. The method of claim 1, wherein providing the information identifying the first degradation estimate of the fluid includes:
   providing the information identifying the first degradation estimate of the fluid to at least one of:
   a display of the machine, or
   a user device.

7. The method of claim 1, wherein providing the information identifying the second degradation estimate of the fluid includes:
   providing the information identifying the second degradation estimate of the fluid to at least one of:
   a display of the machine, or
   a user device.

8. A fluid degradation monitoring system, comprising:
   one or more memories; and
   one or more processors, communicatively coupled to the one or more memories, configured to:
      determine a first degradation estimate of a fluid of a machine using a first technique,
         wherein the first technique is based on one or more characteristics relating to an operation of the machine;
      detect a transition in a value of a dielectric constant of the fluid from a first phase to a second phase based on an average of the value of the dielectric constant decreasing over a first time period of the first phase and the average of the value of the dielectric constant increasing over a second time period of the second phase; and
      determine, after detecting the transition in the value of the dielectric constant, a second degradation estimate of the fluid using a second technique,
         wherein the second technique is based on one or more characteristics relating to the fluid.

9. The fluid degradation monitoring system of claim 8, wherein the fluid is an engine lubricant.

10. The fluid degradation monitoring system of claim 8, wherein the one or more processors are further configured to:
    detect a type of the fluid,
       wherein the first technique is based on the one or more characteristics relating to the operation of the machine and based on the type of the fluid, and
       wherein the second technique is based on the one or more characteristics relating to the fluid and based on the type of the fluid.

11. The fluid degradation monitoring system of claim 10, wherein the one or more processors, when detecting the type of the fluid, are to:
  detect the type of the fluid based on a viscosity of the fluid.

12. The fluid degradation monitoring system of claim 8, wherein the one or more characteristics relating to the operation of the machine include one or more of:
  a speed of an engine of the machine,
  a load on the engine of the machine, or
  a temperature of the engine of the machine,
wherein the one or more characteristics relating to the fluid include one or more of:
  a viscosity of the fluid,
  a density of the fluid,
  the dielectric constant of the fluid, or
  a temperature of the fluid.

13. The fluid degradation monitoring system of claim 8, wherein the first degradation estimate of the fluid and the second degradation estimate of the fluid provide an estimate of a remaining useful life of the fluid.

14. The fluid degradation monitoring system of claim 8, wherein the one or more processors are further configured to:
  provide information identifying the first degradation estimate of the fluid to a display of the machine; and
  provide information identifying the second degradation estimate of the fluid to the display of the machine.

15. A machine, comprising:
  an engine;
  a display; and
  a fluid degradation monitoring system, wherein the fluid degradation monitoring system is configured to:
    detect a replacement of a fluid of the engine;
    determine, after detecting the replacement of the fluid, a first degradation estimate of the fluid using a first technique,
      wherein the first technique is based on one or more characteristics relating to an operation of the engine;
    provide information identifying the first degradation estimate of the fluid to the display;
    detect a transition in a value of a dielectric constant of the fluid from a first phase to a second phase based on an average of the value of the dielectric constant decreasing over a first time period of the first phase and the average of the value of the dielectric constant increasing over a second time period of the second phase;
    determine, after detecting the transition in the value of the dielectric constant, a second degradation estimate of the fluid using a second technique,
      wherein the second technique is based on one or more characteristics relating to the fluid; and
    provide information identifying the second degradation estimate of the fluid to the display.

16. The machine of claim 15, wherein the fluid degradation monitoring system is associated with an engine control module of the engine.

17. The machine of claim 15, wherein the one or more characteristics relating to the operation of the engine are obtained from one or more first sensors associated with the engine,
  wherein the one or more characteristics relating to the fluid are obtained from one or more second sensors associated with the fluid.

18. The machine of claim 15, wherein a curve that is fit to the value of the dielectric constant has a decreasing slope over the first time period and an increasing slope over the second time period.

19. The machine of claim 15, wherein the one or more characteristics relating to the operation of the machine include one or more of:
  a speed of the engine of the machine,
  a load on the engine of the machine, or
  a temperature of the engine of the machine,
wherein the one or more characteristics relating to the fluid include one or more of:
  a viscosity of the fluid,
  a density of the fluid,
  the dielectric constant of the fluid, or
  a temperature of the fluid.

20. The machine of claim 15, wherein the fluid degradation monitoring system is further configured to:
  provide the information identifying the first degradation estimate of the fluid and the information identifying the second degradation estimate of the fluid to a user device.

* * * * *